United States Patent [19]

McConchie et al.

[11] Patent Number: 5,068,401

[45] Date of Patent: Nov. 26, 1991

[54] METHOD FOR PREPARING ORGANIC ESTERS FROM HALOCARBONS AND ALKALI METAL CARBOXYLATES

[75] Inventors: Garnet E. McConchie; Frank E. Mark, both of Stade; Hans-Günter Hollmann, Dollern, all of Fed. Rep. of Germany

[73] Assignee: The Dow Chemical Company, Midland, Mich.

[21] Appl. No.: 943,977

[22] Filed: Dec. 18, 1986

[30] Foreign Application Priority Data

Dec. 21, 1985 [DE] Fed. Rep. of Germany ....... 3545583

[51] Int. Cl.$^5$ ............................................ C07C 67/035
[52] U.S. Cl. .................................................. 560/236
[58] Field of Search .......................................... 560/236

[56] References Cited

U.S. PATENT DOCUMENTS 3,418,360 12/1968 Schulz et al. ...................... 560/236
3,655,701 4/1972 Darre .................................. 560/236
3,968,177 7/1976 Kaufhold et al. ................... 560/236

Primary Examiner—Jose Dees

[57] ABSTRACT

Organic esters such as propylene glycol diacetate are prepared in a single organic reaction phase from the corresponding halocarbon having from 3 to 8 carbon atoms, e.g., 1,2-dicholorpropane and the alkali or alkaline earth metal salt of a carboxylic acid. The inorganic salt formed thereby is not soluble in the organic phase. The reaction rate and selectivity are surprisingly good when the reaction contains little or no water.

1 Claim, No Drawings

METHOD FOR PREPARING ORGANIC ESTERS FROM HALOCARBONS AND ALKALI METAL CARBOXYLATES

BACKGROUND OF THE INVENTION

This invention relates to a method for preparing carboxylic acid esters from halocarbons, more particularly to the preparation of carboxylic acid esters by reacting a halocarbon with a salt in an organic liquid.

Carboxylic acid esters (including mono-, di, and higher esters) such as propylene glycol diacetate, allyl acetate and glycerine triacetate are useful as solvents, lacquers, plasticizers and the like in a variety of commercial applications. For example, glycerine triacetate is used in the treatment of acetate fibers for cigarette filters. Other esters are useful as retarder solvents in high baked automotive coatings, as coalescing agents in aqueous and solvent based paints, as effective cleaning agents in polyester resin cleaning equipment and to harden core sands used in foundry industry.

There are a variety of commercially employed methods for synthesizing organic esters, diesters and triesters. For example, in the preparation of carboxylic acid esters, it is known that alcohols will react with a carboxylic acid anhydride, a carboxylic acid or their combination, in the presence of an acid catalyst such as sulfuric or hydrochloric acid, to form a carboxylic acid ester. Unfortunately, the acid catalyst water as well as a variety of by-products in the resulting reaction product often make recovery of the desired reaction product difficult.

Several alternative methods have been proposed for preparing an organic diester. One such method is described in U.S. Pat. No. 2,115,905. In the described method, a glycol diester is prepared by reacting an alkylene dichloride and an alkali or alkaline earth metal salt of a fatty acid in the presence of a small amount of water. Unfortunately, the described reaction comprises a two phase reaction mixture, i.e., one phase comprising the carboxylic acid salt and the other phase comprising the alkylene dichloride, which results in mixing and handling difficulties as well as reduced organic ester selectivity. In addition, further increases in the yield of the glycol diesters are desired.

Alternatively, U.S. Pat. No. 3,461,156 describes a method for producing carboxylic acid esters by reacting the corresponding acid with a halocarbon in the presence of an alkali metal hydroxide and a mutual solvent consisting of dimethylformamide (DMF), dimethyl sulfoxide (DMSO) or mixtures of the two. The solvent may also comprise water The amounts of water in the DMF and DMSO affect the yield of the carboxylic acid ester, with a solvent having from 10 to 25 percent by volume water being preferred. Unfortunately, the stated yields and product purification processes are commercially undesirable.

Yet another method for preparing a glycol ester is described in U.S. Pat. No. 4,298,758. The method comprises reacting a dichloroisopropyl ether with a carboxylic acid and an alkali metal salt thereof. Unfortunately, due to cleavage of the ether, the reaction product is a mixed reaction product comprising a major portion of dipropylene glycol diacetate and a smaller portion of propylene glycol diacetate. In addition, the monoacetate of propylene glycol and 1-chloro-1-acetoxy-bis(2,2-oxy-propane) are present in the reaction product.

In German Patent 41,507, it is taught that benzyl chloride or ethylene dichloride can be reacted with sodium acetate in acetic acid. In the example of this German patent, the reaction of ethylene dibromide with sodium acetate is described in more detail. With benzyl chloride, however, high reactivity naturally produces high yields that are not obtainable with aliphatic halocarbons. Ethylene dichloride does not tend to produce undesired by-products like halocarbons with more carbon atoms. Furthermore, there is no mention of the criticality to remove water from the reaction mixture since it is not important with these two halocarbons.

Propylene glycol diacetate is produced according to a known, commercially used, process by reacting propylene oxide and water to give propylene glycol which is then converted with acetic acid to propylene glycol diacetate. Glycerol triacetate is commercially produced by reacting glycerol and acetic acid. The commercial processes are disadvantageous since valuable propylene oxide and glycerol are required as starting materials.

In view of the stated deficiencies of the prior art methods for preparing carboxylic acid esters from halocarbons, it remains highly desirable to provide a method for effectively preparing an organic ester at relatively high yields from inexpensive starting materials.

SUMMARY OF THE INVENTION

The present invention is a method for preparing an organic ester from its corresponding halocarbon which method comprises contacting an aliphatic halocarbon having from 3 to 8 carbon atoms with an alkali metal salt of a carboxylic acid within a single phase reaction medium containing an organic liquid reaction diluent in proportions and under conditions sufficient to form the organic ester and an inorganic salt which is insoluble within the reaction diluent.

Surprisingly, it is found that the carboxylic acid ester can be prepared at unexpectedly high yield (unexpectedly high balance of selectivity and conversion) by reacting the described halocarbon having from 3 to 8 carbon atoms with a carboxylic acid salt in the described organic liquid reaction diluent. Accordingly it is indeed surprising that aliphatic halocarbons having 3 or 4 carbon atoms such as 1,2-dichloropropane can be subjected to a similar reaction as ethylene dibromide or ethylene dichloride.

Moreover, the high yield can be obtained without using a catalyst. The inorganic salt formed by the reaction is insoluble in the organic liquid and can easily be removed by filtration or centrifugation.

When organic esters are produced from their corresponding halocarbons, a side reaction is the elimination of a hydrogenhalide, e.g., HCl. It is known that elimination reactions of 1,2-dichloropropane yielding the thermodynamically very stable and undesirable chloropropenes are much more probable than the elimination reaction of ethylene chloride or bromide.

Since the reaction proceeds using the method according to the invention without the production of significant amounts of by-products, once the inorganic salt has been removed, the desired carboxylic acid ester is readily recovered at high purity using distillation techniques.

The method of the present invention is particularly suitable for the preparation of mono-, di- or triesters with the halocarbon reactant being selected accordingly.

The method of the present invention provides the possibility of producing propylene glycol diacetate from a side product, i.e., 1,2-dichloropropane, of the propylene oxide process instead of from the valuable propylene oxide. The method of the present invention also provides the possibility of producing glycerol triacetate from an undesired side product of the glycerol process instead of from glycerol.

DETAILED DESCRIPTION OF ILLUSTRATIVE EMBODIMENTS

The halocarbon reactants suitably employed in the method of the present invention are saturated or unsaturated halocarbons having from 3 to 8, preferably 3 or 4, carbon atoms. The halocarbons preferably have from 1 to 4, most preferably from 1 to 3, substituent halogen atoms. The halogen atoms are preferably chlorine or bromine, most preferably chlorine. The halocarbon reactants should be free of ether linkages which produce undesirable by-products. Representative of suitable halocarbons are 1,2-dichloropropane, 1,2-dichlorobutane, allyl chloride, 1-chloropropane, 1,2,3-trichloropropane, 1-chlorobutane, 2-chloropropane, 2,3-dichloropropene, 3,3-dichloropropene, and 3-chlorobutene-1. Preferred halocarbon reactants for use in the practice of the present invention include 1,2-dichloropropane, allyl chloride, 1,2-dichlorobutane and 1,2,3-trichloropropane. Of the preferred halocarbons, 1,2-dichloropropane is the most preferred starting material in the process of the present invention.

In addition to its preferred utility in the claimed invention, it is also desirable to use 1,2-dichloropropane because of its availability as a side product in the propylene oxide production according to the chlorohydrin process. As evidenced by *Ullmann's Enzyklopadie der Technischen Chemie*, 4th Edition, Volume 19, pages 474 to 480, the capacity of the propylene oxide plants was more than 1 million tons in 1980 in Western Europe, where 690,000 tons were produced according to the chlorohydrin process (page 480, Table 2). Also 5 to 11 percent dichloropropane was produced as a side product, based on the weight of produced propylene oxide (page 474 and FIG. 6 on page 476), i.e., between 34,500 and 76,000 tons of dichloropropane were produced as a side product in 1980. This side product, however, does not have a high commercial use and is often burned as a waste product. The burning of these huge amounts of side products is highly disadvantageous. Similarly, when producing glycerol commercially by reacting glycerol and acetic acid, 1,2,3-trichloropropane is produced as an unwanted side product. Therefore, there exists a long felt need to produce useful products from dichloropropane and 1,2,3-dichloropropane. The carboxylic acid esters such as propylene glycol diacetate and glycerol triacetate produced by the method of this invention are such useful products.

Preferred carboxylic acid salts are the alkali metal and alkaline earth metal salts of a carboxylic acid having form 2 to 6 carbon atoms, most preferably from 2 to 3 carbon atoms. In general, the carboxylic acid salt is advantageously an alkali metal salt of a carboxylic acid having from 2 to 3 carbon atoms, with a sodium salt or potassium salt of a carboxylic acid having from 2 to 3 carbon atoms being more preferred. Most preferably, the sodium salts of acetic acid or propionic acid are employed as carboxylic acid salts in the practice of the present invention.

The halocarbon and carboxylic acid salt are reacted in an organic liquid. Suitable organic liquids useful as the reaction medium in the practice of the present invention are those organic liquids which are capable of forming a single liquid phase with the halocarbon and the carboxylic acid salt and in which the inorganic salt formed by the reaction of the halocarbon with the carboxylic acid salt is insoluble. As used herein regarding the inorganic salt and the organic liquid, the term "insoluble" means that less than about 2 weight percent of the salt will dissolve in the organic liquid, based on the weight of the liquid, preferably less than about 1 percent, more preferably less than 0.5 percent. Although the specific organic liquid most advantageously employed as the reaction medium herein is dependent on the specific halocarbon and carboxylic acid salt employed and the inorganic salt formed upon their reaction, it is generally preferred to use the carboxylic acid, in acid form, which corresponds to the carboxylic acid salt employed. For example, if sodium acetate is employed in preparing the organic esters, acetic acid is most preferably employed as the organic liquid reaction diluent.

Alternatively, but less preferably, organic liquids which are inert to the reactants at the conditions of the reaction and which otherwise meet the requirements of a suitable reaction diluent can also be employed. For example, various glycols, glycol ethers and glycol esters can be employed as the organic liquid reaction medium. In general, however, using these liquids reduces the conversion of the reaction. When a carboxylic acid is employed as the organic liquid reaction medium, it does not act as a true diluent in that the acid and the acid salt are capable of being dissociated. Therefore, it is generally preferable to employ a carboxylic acid which corresponds to the carboxylic acid salt as this will not lead to mixed esters with a coincident decrease in selectivity.

The amounts of the carboxylic acid salt and halocarbon, as well as the amounts of the organic liquid reaction medium, employed in the practice of the present invention are dependent on a variety of factors including the specific halocarbon, carboxylic acid salt and organic liquid employed, the desired degree of conversion of the halogen atoms to ester groups, and the conditions at which the reaction is conducted. Preferably, the carboxylic acid salt and halocarbon are employed in proportions such that the reaction mixture contains from about 0.1 to about 1.5 equivalents of the carboxylic acid salt per equivalent of halocarbon, wherein a halocarbon equivalent is the number of reactive halogen atoms per molecule of the halocarbon. Preferably, the reaction mixture contains from about 0.25 to about 1.2, more preferably from about 0.3 to about 1.0 equivalents, of the carboxylic acid salt for each equivalent of the halocarbon. Most preferably, the halocarbon is employed in stoichiometric excess of two to three molar when compared to the carboxylic acid salt. Surprisingly, it is found in the case of dihalogenated halocarbons (e.g., dichloropropene) that an excess of chlorinated hydrocarbon does not yield substantial amounts of the mono ester, which would be expected.

The organic liquid reaction medium is employed in amounts sufficient to form a single liquid phase with the carboxylic acid salt and the halocarbon. Alternatively, the carboxylic acid salt can be employed in excess amounts which exceed the solubility of acid salt in the organic liquid. Then, as the reaction proceeds, the undissolved (i.e., excess) amounts of acid salt dissolve due to the reaction of the solubilized carboxylic acid salt with the halocarbon. The amount of the organic liquid employed will vary depending on the specific organic liquid, as well as the specific halocarbon and carboxylic acid salt employed, the solubility of the carboxylic acid salt and halocarbon in the organic liquid, and the conditions of reaction. In general, for economic reasons, the amount of organic liquid is employed in an amount such that the carboxylic acid salt forms at least a 5, preferably at least a 10, weight percent solution in the organic liquid. In general, the carboxylic acid salt is completely dissolved in the organic liquid and the minimum amounts of the organic liquid employed are thus limited to the saturation point of the carboxylic acid salt in the organic liquid at the temperatures of operation. For example, sodium acetate will form about a 55 weight percent solution in acetic acid at 180° C. and the concentration of the sodium acetate is selected accordingly. In general, the organic liquid reaction diluent is employed in an amount sufficient to form from a 10 to 85 weight percent solution of the carboxylic acid salt, most preferably from 15 to 75 weight percent solution of the carboxylic acid salt.

The presence of low amounts of water in the reaction mixture has also been found to significantly affect the rate and selectivity of the reaction. Specifically, water in the reaction mixture, although increasing the rate of reaction, will more significantly decrease the selectivity of the reaction. Most preferably, the amounts of water in the reaction mixture are minimized, with no measurable amount of water being most preferred. However, in commercial operation, it is often impractical and/or impossible to eliminate water from the reaction mixture and up to about three weight percent water based on the total weight of the reaction mixture can be tolerated while still achieving a desirable selectivity. More preferably, the reaction mixture contains less than about 0.5, most preferably less than 0.2, weight percent water.

In conducting the reaction to prepare the desired organic ester, the halocarbon, carboxylic acid salt and organic liquid are mixed and subjected to an elevated temperature and pressure sufficient to cause reaction. The temperature and pressure most advantageously employed in conducting the reaction are dependent on a variety of factors including the specific reactants and organic liquid reaction diluent employed and the desired reaction times. For example, the temperature of reaction has been found to affect the rate and selectivity of the reaction. In general, temperatures from about 160° C. to about 300° C. are advantageously employed to give a reasonable rate of reaction (e.g., 90 percent or more conversion in 12 hours or less) coupled with a high selectivity (e.g., selectivity of more than 80 percent). Preferably, temperatures from about 160° C. to about 300° C. are employed in conducting the reaction, particularly in the preparation of organic diesters. Higher temperatures have been found to reduce selectivity due to the competing elimination reaction and the formation of monoesters. More preferably, the reaction is conducted at a temperature from about 170° C. to about 280° C. and most preferably from 180° C. to 260° C.

The reaction is conducted for a period sufficient to obtain the desired conversion. In general, reaction times will vary from about 0.1 to about 12 hours, with the shorter reaction times generally being employed using higher reaction temperatures. Preferably, the reaction will be conducted for a period of form 0.5 to 8 hours, with a temperature of reaction being selected to provide desired yields within these reaction times. Preferably more than 99 percent of the used salt of the carboxylic acid should have been reacted.

In general, the reaction is conducted in a closed reactor under a pressure greater than or equal to the vapor pressure of the contents.

In conducting the reaction, the halocarbon, carboxylic acid salt and organic liquid are advantageously mixed, preferably continuously mixed during reaction. A good mixing of the components is preferred since it has been found that better mixing will reduce the time required for the desired reaction.

Following complete reaction and removal of the precipitated inorganic salt formed by the reaction, the desired organic ester is easily recovered, at desired purity, using distillation techniques. For example, due to the significant temperature differences normally encountered in the boiling points between the halo-carbon, organic liquid reaction diluent and the carboxylic acid ester product, distillation techniques are very often advantageously employed for such recovery. For example, the carboxylic acid ester can be separated at a purity of 99 percent or more using distillation techniques. The reaction diluent and the unreacted halocarbon are removed from the distillation column as an azeotropic mixture and recycled into the reaction. Low boiling by-products are recovered from the distillation column. Preferably, at the end of the reaction, the reaction mixture should not contain unreacted salt of the carboxylic acid to avoid its precipitation during the distillation as a result of the removal of the reaction diluent.

In addition to the desired carboxylic acid ester, the recovered product will contain only small amounts of by-products which can be formed during reaction of the halocarbon and carboxylic acid salt which include monoester or elimination products formed by dehydrogenation.

The following examples are presented to illustrate the invention and should not be construed to limit its scope. In the examples, all parts and percentages are by weight, unless otherwise indicated.

EXAMPLE 1

Into a suitably sized, lined pressure container equipped with an agitator and heating and cooling means is added 180 parts of a water-free acetic acid (i.e., the acetic acid contains less than 1 percent water), 82 parts of sodium acetate and 180 parts of 1,2-propylene dichloride.

The mixture is then heated to 200° C. and stirred continuously while maintaining this temperature for a period of 6 hours. At this time, the selectivity of the reaction based on the amount of reacted propylene dichloride which forms propylene glycol diacetate (PGDA) is greater than 80 percent calculated from the amount of sodium acetate used. Based on the amounts of sodium chloride found in the reaction product, the conversion is above 90 percent of the sodium acetate added.

Following the reaction, the reaction mixture is cooled to room temperature and filtered to remove the sodium chloride formed by the reaction. The salt-free filtrate contains acetic acid, propylene dichloride, propylene glycol diacetate, monochloropropenes and trace amounts of other materials. The resulting reaction mixture is distilled and a propylene glycol diacetate containing reaction product is separated. This product has greater than 99 percent purity and a boiling temperature of 190° C.

When the foregoing reaction is duplicated, except that the reaction mixture contains 1 percent water based on the total weight of reaction mixture, the selectivity of the reaction to propylene glycol diacetate remains above 70 percent. As the amounts of water in the reaction mixture are increased, the selectivity is found to significantly decrease. Specifically, when the reaction mixture contains 5 percent of water, the selectivity to propylene glycol diacetate is reduced to 50 percent. When the reaction mixture contains 10 percent water, the selectivity is reduced further to 40 percent, whereas at 33 percent water, the selectivity of propylene dichloride to propylene glycol diacetate is only 27 percent based on propylene dichloride.

EXAMPLE 2

Into the pressure container used in Example 1 is added 180 parts of sodium acetate and 180 parts of 1,2-propylene dichloride. The mixture is then heated to 200° C. and stirred continuously while maintaining this temperature for a period of 4 hours. At this time the selectivity of the reaction based on the amount of reacted propylene dichloride which forms propylene glycol diacetate (PGDA) is greater than 85 percent calculated from the amount of sodium acetate used. Based on the amounts of sodium chloride separated from the reaction product the conversion is above 99 percent of the sodium acetate added.

Following the reaction, the reaction mixture is cooled to room temperature and filtered to remove the sodium chloride formed by the reaction. The salt-free filtrate contains acetic acid, propylene dichloride, propylene glycol diacetate, monochloropropenes and trace amounts of other materials. The resulting reaction mixture is distilled and a propylene glycol diacetate containing reaction product is separated. This product has greater than 99 percent purity and a boiling temperature of 190° C.

The azeotropic mixture of unreacted 1,2-dipropylene dichloride and acetic acid is recovered from the distillation column and recycled as starting material for further reactions.

EXAMPLE 3

Into the pressure container used in Example 1 is added 180 parts of a water-free acetic acid, 82 parts of sodium acetate and 300 parts of 1,2-propylene dichloride. The mixture is then heated to 200° C. and continuously stirred while maintaining the temperature for a period of 6 hours. The conversion rate of sodium acetate is above 99 percent determined from the amount of sodium chloride separated from the reaction mixture subsequent to cooling to room temperature. The reaction mixture is then distillated as described in Example 2.

EXAMPLE 4

To a reaction vessel identical to that employed in Example 1 is added 38.3 parts allyl chloride, 41 parts of sodium acetate and 350 parts of acetic acid. This reaction mixture contains 0.5 percent water based on the total weight of the reaction mixture. The reaction mixture is heated, with continuous agitation, at 200° C. for 6 hours. The amount of sodium acetate reacted (i.e., the conversion) is found to be above 90 percent. The selectivity is also above 90 percent. Using conventional distillation techniques, a product consisting of allyl acetate is recovered at a purity greater than 99 percent.

EXAMPLE 5

To a reaction vessel identical to that employed in Example 1 is added 54 parts of sodium propionate, 297 parts of propionic acid and 63 parts of 1,2-propylene dichloride. This reaction mixture contains less than 0.5 percent water. It is heated at 200° C., with continuous agitation, for a period of 6 hours. At that time, the conversion of sodium propionate is greater than 80 percent. Using conventional distillation techniques, a product containing propylene glycol dipropionate, at a purity of greater than 99 percent, is recovered. The total yield of propylene glycol dipropionate based on the amounts of sodium propionate originally added to the reaction vessel is greater than 65 percent.

EXAMPLE 6

To a reaction vessel identical to that employed in Example 1 is added 82 parts of sodium acetate, 147 parts of 1,2,3-trichloropropane and 180 parts acetic acid. This mixture which contains less than 0.5 percent water is heated to a temperature of 180° C. and maintained at this temperature, with continuous agitation, for a four-hour period. At the end of this period, the reaction is terminated. The yield of 1,2,3-triacetoxypropane, based on the amount of sodium acetate originally added to the reaction vessel is greater than 70 percent at a conversion of sodium acetate which is greater than 95 percent.

What is claimed is:

1. A method for preparing an organic ester from its corresponding halocarbon which method comprises contacting an aliphatic halocarbon selected from the group consisting of 1,2-dichloropropane or 1,2,3-trichloropropane with a sodium salt of acetic or propionic acid within a single phase reaction medium containing acetic acid or propionic acid in proportions and at a temperature in the range from about 160° C. to about 300° C. under conditions sufficient to form the organic ester and an inorganic salt which is insoluble within the acetic acid or propionic acid.

* * * * *